United States Patent [19]

Amir

[11] Patent Number: 5,048,965
[45] Date of Patent: Sep. 17, 1991

[54] THREE-DIMENSIONAL IMAGING TECHNIQUE WITH OCCLUSION AVOIDANCE

[75] Inventor: Israel Amir, Ewing, N.J.
[73] Assignee: AT&T Bell Laboratories, Murray Hill, N.J.
[21] Appl. No.: 517,779
[22] Filed: May 2, 1990
[51] Int. Cl.$^5$ .............................................. G01B 11/24
[52] U.S. Cl. .................................... 356/376; 382/41; 382/8
[58] Field of Search ....................... 356/376, 237, 394; 382/41, 8, 48; 250/561–563

[56] References Cited

U.S. PATENT DOCUMENTS

| 4,502,785 | 3/1985 | Truax | 356/376 |
| 4,538,909 | 9/1985 | Bible et al. | 356/237 |
| 4,653,140 | 3/1987 | Tamura | 356/376 |
| 4,731,860 | 3/1988 | Wahl | 382/41 |
| 4,811,410 | 3/1989 | Amir et al. | 356/327 |
| 4,929,845 | 5/1990 | Amir et al. | 250/561 |
| 4,965,665 | 10/1990 | Amir | 356/373 |

OTHER PUBLICATIONS

B. Carrihill and R. Hummel, "Experiments with the Intensity Ratio Depth Sensor," *Computer Vision, Graphics, and Image Processing*, 32, 337–358 (1985).

Primary Examiner—Richard A. Rosenberger
Assistant Examiner—Hoa Pham
Attorney, Agent, or Firm—R. B. Levy

[57] ABSTRACT

A three-dimensional image of the features on a surface (21) of a substrate (22) is obtained by first spanning the surface with a pair of lines of light (42 and 44), each directed from opposite sides to illuminate each of successive pairs of spaced-apart stripes (46,48) of surface area. The intensity of the light reflected from each successive strip (27) contiguous to, and lying between, the strips illuminated by the first lines of light is sensed. The surface (21) is next spanned with a second pair of lines of light (58,60) directed from opposite sides. The intensity of light reflected from each successive strip contiguous to, and lying between, the successive strips illuminated by the second pair of lines of light is sensed. A three-dimensional image of the substrate surface can be obtained from a prescribed relationship between the two sensed intensities.

7 Claims, 1 Drawing Sheet

THREE-DIMENSIONAL IMAGING TECHNIQUE WITH OCCLUSION AVOIDANCE

TECHNICAL FIELD

This invention relates to a method and apparatus for obtaining a three-dimensional image of a substrate with reduced incidence of occlusion of topographical features on the substrate surface.

BACKGROUND OF THE INVENTION

Within the electronics industry, there is a trend towards automated inspection of a circuit board following placement of components on it to detect if any of the components have been improperly placed or are missing. Further, efforts are now underway to inspect the circuit board before component placement but immediately after application of a layer of solder paste, which is applied to bond the components, to detect if the paste has been properly applied. By inspecting the circuit board at each stage of its fabrication, the board can be repaired to correct such defects more economically. For example, if the solder paste has been applied improperly, it is far easier, and hence less expensive, to clean the board and reapply paste to it prior to placement of the components rather than afterwards. Similarly, missing and misplaced components can be corrected more easily if such defects are detected prior to reflow of the solder paste to solder bond the components to the circuit board rather than after reflow of the paste.

In my co-pending application "Three-Dimensional Imaging Using Sharp Gradient of Illumination", Ser. No. 440,948, filed on Nov. 24, 1989, and assigned to AT&T (herein incorporated by reference), there is disclosed a three-dimensional imaging system especially suited for circuit board inspection. The imaging system described in my co-pending application comprises a linescan camera positioned so its optical axis is generally perpendicular to the surface of a circuit board to capture the image of a single strip of area on the board surface. Each of a pair of light sources is separately energized to generate a line of light directed at the surface of the circuit board from the same side, at substantially the same angle, to illuminate a strip of area on the board surface. While each light source is energized, a relative motion is imparted between the linescan camera and the circuit board so that the camera senses the intensity of the light reflected from successive strips of area on the board surface. The ratio of the reflectance intensities measured when the circuit board is illuminated with each of the two light sources yields a measure of the height of the topographical features within each successive strip. From the height information, a three-dimensional image of the circuit board can be obtained.

While the above-described technique enables a three-dimensional image of a substrate to be obtained in a very efficient manner, the technique, as with other similar types of triangulation techniques for three-dimensional imaging, does incur a drawback which limits its effectiveness. When a relatively tall topographical feature, such as a component, is situated in close proximity to a short feature, such as a component or solder paste deposit, the taller feature may occlude (shadow) the shorter one depending on the direction of the light. As a consequence, an accurate measurement of the height of the shorter feature may be difficult to ascertain, thus adversely affecting the resultant three-dimensional image of the circuit board.

Thus, there is a need for a technique for obtaining a three-dimensional image of a substrate with reduced incidence of occlusion.

SUMMARY OF THE INVENTION

Briefly, in accordance with a preferred embodiment of the invention, a technique is provided for obtaining a three-dimensional image of a substrate with reduced incidence of occlusion of shorter features by taller features. The method is initiated by spanning the substrate with a first pair of lines of electromagnetic radiation, typically lines of light, with the lines of each pair directed at the substrate from opposite sides at an acute angle. The lines of light serve to illuminate successive pairs of spaced-apart strips of area on the substrate surface. The intensity of the light reflected from the strip of area lying between each successive pair of strips illuminated by the lines of light is sensed by a linescan camera which is likewise spanned across the substrate. Thereafter, the substrate is spanned with a second pair of lines of light, directed at the substrate from opposite directions at an acute angle, to illuminate the same successive pairs of spaced strips. The intensity of light reflected from the strip lying between the successive pairs of strips illuminated by the second pair of lines of light is sensed by the linescan camera as before. The height of the features in each successive strip is obtained in accordance with a prescribed relationship between the measured intensity attributed to the first pair of lines of lights to the intensity attributed to the second pair.

DETAILED DESCRIPTION

Figure 1:
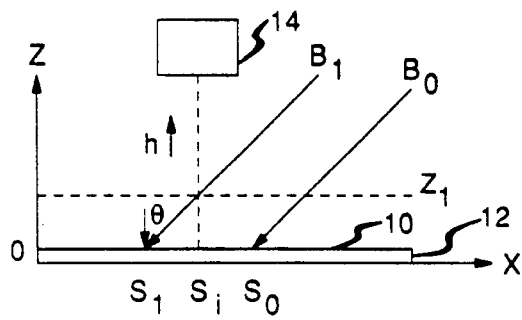
FIG. 1 is side view of a substrate illuminated by each of a pair of light beams.

Before describing the three-dimensional imaging system of the present invention, a brief summary of the principle of three-dimensional imaging using a sharp gradient of illumination will be described. For a more detailed discussion of this technique, reference should be had to my aforementioned co-pending application, Ser. No. 440,948, herein incorporated by reference. FIG. 1 shows a side view of a substrate 10, such as a circuit board or the like, having a major surface 12. Each of a pair of light beams $B_0$ and $B_1$ is directed at approximately the same angle ($\theta$), measured with respect to a line normal to the surface 12, to illuminate each of a pair of spots $S_0$ and $S_1$, respectively. The beams $B_0$ and $B_1$ have the same intensity profile, which for the sake of simplicity is assumed to be linear. In other words, the transmission intensity gradient of each of the beams $B_0$ and $B_1$ is assumed to drop off linearly from the center of the beam. (In actuality, the transmission gradient may not be truly linear, but other solutions exist for other illumination profiles as will be discussed hereinafter.)

When a light-sensing mechanism 14 (e.g., a photocell or the like) is trained on a spot $S_i$ on the surface 12, the intensity of the light reflected into the sensor will depend on the spacing of the spot $S_i$ from the spots $S_0$ and $S_1$. The closer the spot $S_i$ is to a separate one of the spots $S_0$ and $S_1$, the greater the influence of the intensity of the beams $B_0$ and $B_1$, respectively, on the intensity of the spot $S_i$ measured by the sensor 14. Conversely, as the lateral distance between the spot $S_i$ and a separate one of the spots $S_0$ and $S_1$ increases, there will be a corresponding decrease in the measured intensity of the spot $S_i$ attributed to a separate one of the beams $B_0$ and $B_1$, respectively.

As discussed in my co-pending patent application, if $I_0$ and $I_1$ are the reflectance intensity measured at the spot $S_i$ attributable to a separate one of the beams $B_0$ and $B_1$, respectively, then the Z axis position of the spot will be given by the formula $$Z = \frac{1}{C} \cdot \frac{I_0 - I_1}{I_0 + I_1} + Z_0 \tag{1}$$

where C is a constant and $Z_0$ is the position of the origin (assumed to be zero). By separately spanning each of a pair of lines of light $B_0$ and $B_1$ across the surface 12 to illuminate successive strips of area, and by measuring the reflectance intensity of a strip adjacent to the one being illuminated, a three-dimensional image of the substrate 10 can be obtained as taught in my co-pending application.

Figure 2:
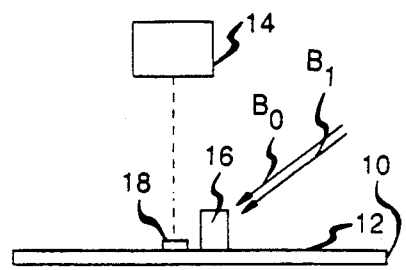
FIG. 2 is an enlarged view of the substrate of FIG. 1 showing the manner in which a tall feature thereon may occlude a shorter feature.

Notwithstanding the ability of the imaging technique of my co-pending application to obtain such a three-dimensional image in an efficient manner, I have discovered a technique for overcoming the disadvantage of occlusion inherent in conventional three-dimensional triangulation imaging techniques. As seen in FIG. 2, with my previous three-dimensional imaging technique, the lines of light $B_0$ and $B_1$ are separately spanned across the surface 12 in the same direction. In other words, each of the lines $B_0$ and $B_1$ separately illuminate the successive strips of area on the surface 12 from the same side. The disadvantage incurred by doing so is that a relatively tall feature 16, such as a component, will likely occlude (shadow) a relatively short feature 18, one in close proximity to the tall one. As a consequence, the measured reflectance intensity will likely be inaccurate, yielding an incorrect three-dimensional image.

Figure 3:
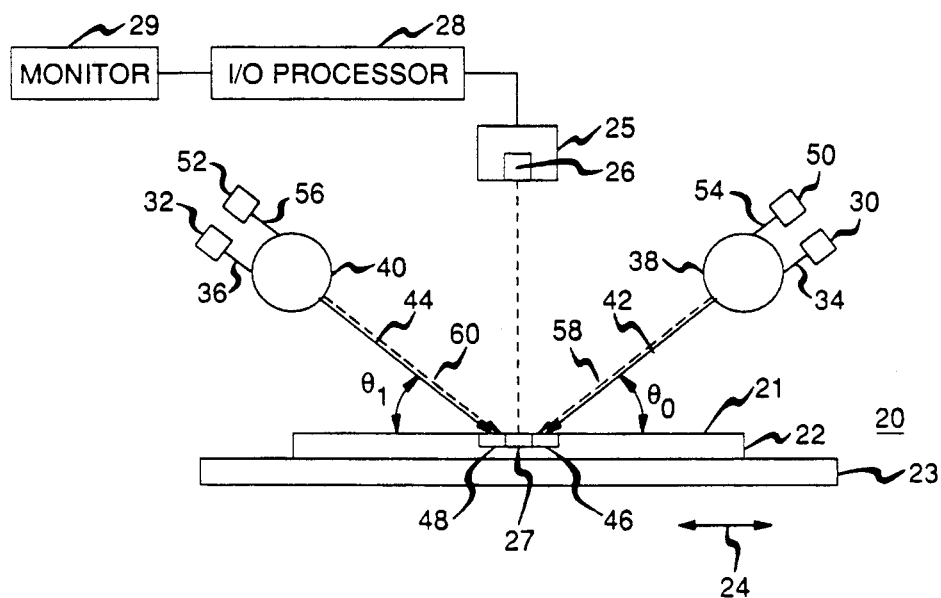
FIG. 3 is a schematic diagram of a system, in accordance with the present invention, for obtaining a three-dimensional image of the substrate of FIG. 1.

Referring now to FIG. 3, there is shown a block schematic diagram of an apparatus 20, in accordance with a preferred embodiment of the present invention, for obtaining a three-dimensional image of a major surface 21 on a substrate 22, such as circuit board, with reduced incidence of occlusion. The system 20 comprises an x table 23 for reciprocating the substrate back and forth along an axis 24. Overlying the substrate 22 is a linescan camera 25 within which is a plurality of charge-coupled devices (CCD's) 26 arranged in a linear array extending into the plane of the drawing so as to be perpendicular to the axis 24. Each CCD 26 serves to image a small area (pixel) on the substrate surface 21, and thus the CCD's collectively serve to capture the image of a thin strip of area 27 running accross the surface perpendicular to the axis 24. An image processor 28, identical to that described in U.S. Pat. No. 4,811,410, issued on Mar. 7, 1989, in the name of Israel Amir et al., and assigned to AT&T, is coupled to the linescan camera 25 to process its output signal to establish the intensity of light reflected into the camera. A monitor 29 is coupled to the image processor 28 to display output information produced by the image processor.

A first pair of light sources 30 and 32 is situated above the substrate 20 so each lies on an opposite one of the sides of the linescan camera 25. The light sources 30 and 32 produce identical profile beams 34 and 36, respectively (shown as solid lines), which are directed through a separate one of a pair of cylindrical lenses 38 and 40. As each of the beams 34 and 36 passes through a separate one of the lenses 38 and 40, respectively, the beam is refracted into a line of light 42, 44 (shown in solid), whose longitudinal axis extends into the drawing perpendicular to the axis 24. Each of the lines of light 42 and 44 is directed at the surface 21 of the substrate 22 from opposite sides at an angle $\theta_0$ and $\theta_1$, respectively, to illuminate a separate one of a pair of strips 46 and 48, contiguous to, and lying on, opposite sides of the strip 27 imaged by the linescan camera 25.

Like the light sources 30 and 32, each of a second pair of light sources 50 and 52 is situated above the substrate 20 on opposite sides of the linescan camera 25. Each of the light sources 30 and 32 produces a separate one of a pair of identical profile beams 54 and 56 (shown by dashed lines) which are directed into a separate one of the lenses 38 and 40. As each of the beams 54 and 56 passes through a separate one of the lenses 38 and 40, respectively, the beam is refracted and becomes a line of light 58, 60. The lines of light 58 and 60, like the lines of light 42 and 44, are directed at the substrate surface 21 from opposite sides to illuminate a separate one of the strips 46 and 48. In practice, the angle between each of the lines of light 58 and 60 and the surface 21 is substantially equal to $\theta_0$ and $\theta_1$, respectively, the angle between of each of the first lines of light 42 and 44, respectively, and the substrate surface.

Figure 4:
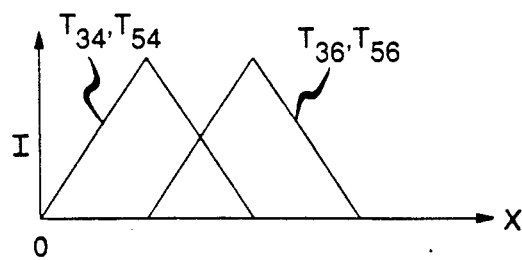
FIG. 4 is a plot of the intensity profiles of each of a pair of light sources of the system of FIG. 3.

For purposes of simplicity, it is assumed that the beams 34 and 36 have linear intensity profiles as indicated in FIG. 4. In other words, the intensity profile of the beams 34 and 36 ($T_{34}$ and $T_{36}$, respectively) falls off linearly as a function of the lateral distance (along the x axis) from the center of the beam. (It should be understood that other solutions exist for non-linear profiles.) Consequently, the lines of light 42 and 44 produced by the beams 34 and 36, respectively, also are assumed to have linear intensity profiles. Likewise, the beams 54 and 56 are assumed to have linear intensity profiles as do their corresponding lines of light 58 and 60, respectively.

In accordance with the teachings of my co-pending application, the z axis distance of a feature in the strip 27 from the linescan camera 25 is a function of the light intensity measured by the camera. The intensity of the light measured by the linescan camera 25 which is attributed to a separate one of the lines of light 42, 44, 58 and 60, is given by a separate one of the relationships:

$$I_{42} = K_1(az+b) \tag{2}$$

$$I_{44} = K_2(az+b) \tag{3}$$

$$I_{58} = K_1(-az-b) \tag{4}$$

$$I_{60} = K_2(-az+b) \tag{5}$$

where the terms $I_{42}$, $I_{44}$, $I_{58}$ and $I_{60}$ are the measured intensity values, a and b are the coefficients of the linear slope and intercept, respectively, obtained from the intensity profile of each line of light, and $K_1$ and $K_2$ are each constants, representing the reflectance associated with the left-hand and right-hand pairs of light sources 32 and 52, and 30 and 50, respectively. Note that the constants $K_1$ and $K_2$ are different because the angle $\theta_0$ is likely to be sufficiently different enough from $\theta_1$ such that the difference in reflectivity must be taken into account.

When the surface 21 is to be spanned with both of the lines of light 42 and 44, then the intensity of the light received by the linescan camera 25 will be given by the relationship:

$$I_{42} + I_{44} = (K_1 + K_2)(az + b) \tag{6}$$

By the same token, when the substrate 22 is spanned by the lines of light 58 and 60, the intensity of the light received by the linescan camera 25 will be given by:

$$I_{58} + I_{60} = (K_1 + K_2)(-az + b) \tag{7}$$

The z term in equations (6) and (7) can be readily extracted by dividing one equation from another and then rearranging terms to obtain:

$$Z = \frac{b}{a}\left[\frac{(I_{42} + I_{44}) - (I_{58} + I_{60})}{(I_{42} + I_{44}) + (I_{58} + I_{60})}\right] \tag{8}$$

The z term given by equation (8) is entirely independent of the reflectivity constants $K_1$ and $K_2$.

As may now be appreciated, the z term, representing the height of the linescan camera 25 from the feature in the strip 27 of FIG. 3, can be readily obtained by first spanning the substrate 20 with the lines of light 42 and 44, then with the lines of light 58 and 60. The spanning of the surface 21 by the lines of light 42 and 44 is accomplished by rendering only the light sources 30 and 36 operative while the x table 23 displaces the substrate 20 along the axis 24. As the substrate 22 is displaced along the axis 24, the intensity sum $I_{42} + I_{44}$ for each pixel imaged by each corresponding CCD element 26 in each successive strip 27 lying between each successive pair of spaced-apart strips 46 and 48 illuminated by the lines of light 42 and 44, respectively, is measured.

Similarly, the spanning of the surface 21 by the lines of light 58 and 60 is accomplished by rendering only the light sources 50 and 52, respectively, operative while the x table 23 displaces the substrate 22 along the axis 24. In this way, the intensity sum $I_{58} + I_{60}$ for each pixel in each successive strip 27, lying between each successive pair of strips 46 and 48 illuminated by the lines of light 58 and 60, respectively, can be measured. Once the intensity sums $I_{42} + I_{44}$ and $I_{58} + I_{60}$ for each pixel in each successive strip 27 have been obtained, the z axis position of the features in each successive strip of area on the surface can be obtained from eq. (8). From the z axis value calculated for each successive strip, a three-dimensional image of the surface 21 can thus be obtained. By spanning the surface 21 with two oppositely directed lines of light, the incidence of occlusion of shorter features by taller ones is greatly reduced. Thus, the resultant three-dimensional image will be more accurate.

The operation of the imaging system 20 described above has been predicated on each of the lines of light 42, 44, 58 and 60 having a linear intensity profile. However, each of the lines of light 40, 42, 58 and 60 need not have a linear intensity profile in order to practice the instant three-dimensional imaging technique. As indicated below by equations (9)–(12), the sensed intensities $I_{42}$, $I_{44}$, $I_{58}$ and $I_{60}$ can be expressed generally a function f (z) of the z axis position of the linescan camera 25.

$$I_{42} = K_1 f_1(z) \tag{9}$$

$$I_{44} = K_2 f_1(z) \tag{10}$$

$$I_{58} = K_1 f_2(z) \tag{11}$$

$$I_{60} = K_2 f_2(z) \tag{12}$$

Equations (6) and (7) can be combined, yielding:

$$I_{42} + I_{44} = (K_1 + K_2) f_1(z) \tag{13}$$

Similarly, equations (11) and (12) can be combined, yielding:

$$I_{58} + I_{60} = (K_1 + K_2) f_2(z) \tag{14}$$

Dividing equation (13) by equation (14) yields:

$$\frac{I_{42} + I_{44}}{I_{58} + I_{60}} = \frac{f_1(z)}{f_2(z)} \tag{15}$$

As long as $f_1(z)/f_2(z)$ is monotonically increasing, a single solution exists.

As described, the surface 21 of the substrate 22 is separately spanned by each of a first pair of lines of light 42 and 44 directed from opposite sides, and with a second pair of lines of light 58 and 60 directed from opposite sides. Rather than span the surface 21 twice with a separate one of two pairs of lines of light 42 and 44 or 58 and 68, the surface 21 could be spanned separately with two or more pairs of lines of light. If multiple pairs of lines of light are indeed employed, equation (8) must be accordingly modified to include the appropriate intensity sums. It is not believed that any advantage would be achieved by separately spanning the surface 21 with more than a single pair of oppositely directed lines of light.

Rather than separately span the surface 21 with the pairs of lines of light 42 and 44 and 58 and 60, other types of electromagnetic radiation could be used, such as microwaves, radar waves or the like. Changing the nature of the radiation directed at the surface 21 would necessitate substituting an appropriate intensity measurement device in place of the linescan camera 25.

The foregoing discloses a technique for imaging the surface 21 of a substrate 22 by separately spanning it with each of a pair of oppositely directed lines of light 42 and 44, and 58 and 60 to determine the z axis position of features in successive strips of area on the surface.

It is to be understood that the above-described embodiments are merely illustrative of the principles of the invention. Various modifications and changes may be made thereto by those skilled in the art which will embody the principles of the invention and fall within the spirit and scope thereof.

I claim:

1. A method for obtaining a three-dimensional image of a substrate, with reduced incidence of occlusion of shorter features on the substrate by taller features, comprising the steps of:

spanning the substrate with a first pair of lines of electromagnetic radiation directed at the substrate from opposite sides so each line irradiates a separate one of a plurality of successive pairs of spaced-apart strips of area on the surface;

sensing the intensity of electromagnetic radiation reflected from each strip of area spaced between each successive pair of spaced-apart strips irradiated by a separate one of the first pair of lines of electromagnetic radiation;

spanning the substrate with a second pair of lines of electromagnetic radiation directed at the substrate from opposite sides so each line irradiates a separate one of the plurality of successive pairs of spaced-apart strips of area on the substrate surface previously irradiated by a separate one of the first pair of lines of electromagnetic radiation;

sensing the intensity of electromagnetic radiation reflected from each strip of area lying between each successive pair of spaced-apart strips irradiated by a separate one of the second pair of lines of electromagnetic radiation; and establishing a three-dimensional image of the substrate in accordance with a prescribed relationship between the intensity of electromagnetic radiation sensed with the substrate is spanned by a first pair of lines of electromagnetic radiation and the intensity of electromagnetic radiation sensed when the substrate is spanned by the second pair of lines of electromagnetic radiation.

2. The method according to claim 1 wherein the first spanning step is carried out by imparting a relative motion between the substrate and a first pair of lines of light directed at the substrate from opposite sides to illuminate a separate one of a pair of spaced-apart strips of surface area and wherein the second spanning step is carried out by imparting a relative motion between the substrate and a second pair of lines of light directed at the substrate from opposite sides to illuminate a separate one of a pair of spaced-apart strips of surface area.

3. The method according to claim 2 wherein each of the first and second pairs of lines of light have linear profiles and wherein the three-dimensional image is established in accordance with a ratio of the difference in the intensities of electromagnetic radiation sensed when the substrate is spanned by the first and second pair of lines of light to the sum of the illumination intensities.

4. Apparatus for obtaining a three-dimensional image of a substrate with reduced incidence of occlusion of short features on the substrate by tall features comprising:

first means for producing each of a first pair of lines of electromagnetic radiation directed at the substrate from opposite sides to irradiate a separate one of a pair of spaced-apart strips of area running across the substrate;

second means producing each of a second pair of lines of electromagnetic radiation directed at the substrate from opposite sides, during intervals other than when the first pairs of lines of electromagnetic radiation are directed at the substrate, to irradiate a separate one of the pair of spaced-apart strips of area running across the substrate;

means for sensing the intensity of electromagnetic radiation reflected from a strip of area contiguous to, and lying between, the strips separately irradiated by each of the first and second pairs of lines of electromagnetic radiation;

means for imparting a relative motion between the substrate, the combination of the electromagnetic radiation-sensing means, and the first and second radiation-producing means so that the substrate is effectively spanned separately by each of the first and second pairs of lines of electromagnetic radiation while the electromagnetic radiation-sensing means senses the electromagnetic radiation reflected from each successive strip contiguous to, and lying between, the successive pairs of strips irradiated by the first and second lines of electromagnetic radiation; and means coupled to the electromagnetic radiation-sensing means for establishing a three-dimensional image of the substrate in accordance with a prescribed relationship between the electromagnetic radiation intensity sensed when the substrate is irradiated with the first pairs of lines of electromagnetic radiation and the radiation intensity when the substrate is irradiated with the second pairs of lines of electromagnetic radiation.

5. The apparatus according to claim 4 wherein the first means for irradiating the substrate with electromagnetic radiation comprises a first pair of light sources, each producing a beam of light directed at the substrate from opposite sides; and a pair of cylindrical lenses, each serving to refract the beam produced by a separate one of the first pair of light sources into a line of light.

6. The apparatus according to claim 5 wherein the second means for irradiating the substrate comprises a second pair of light sources, each producing a beam of light which is directed into a separate one of the cylindrical lenses to produce a separate one of a second pair of lines each directed at the substrate from opposite sides.

7. The apparatus according to claim 6 wherein the means of sensing electromagnetic radiation comprises a linescan camera.

* * * * *